(12) United States Patent
Austria

(10) Patent No.: US 10,299,825 B2
(45) Date of Patent: May 28, 2019

(54) SHARPS BLADE APPLICATOR AND STORAGE DEVICE

(71) Applicant: Aspen Surgical Products, Inc., Caledonia, MI (US)

(72) Inventor: Georgene Austria, West Hills, CA (US)

(73) Assignee: Aspen Surgical Products, Inc., Caledonia, MI (US)

( * ) Notice: Subject to any disclaimer, the term of this patent is extended or adjusted under 35 U.S.C. 154(b) by 133 days.

(21) Appl. No.: 15/295,443

(22) Filed: Oct. 17, 2016

(65) Prior Publication Data

US 2017/0027602 A1    Feb. 2, 2017

Related U.S. Application Data

(63) Continuation of application No. 14/506,554, filed on Oct. 3, 2014.

(51) Int. Cl.
*A61B 17/3215*  (2006.01)
*A61B 17/3217*  (2006.01)

(52) U.S. Cl.
CPC ...... *A61B 17/3215* (2013.01); *A61B 17/3217* (2013.01)

(58) Field of Classification Search
CPC ....... B65D 83/10; B26B 5/006; B26B 11/003; B26B 1/08; A61M 5/002; A61B 50/3001;
(Continued)

(56) References Cited

U.S. PATENT DOCUMENTS 334,981 A    1/1886 Rampe, Jr.
1,002,468 A    9/1911 Strangman
(Continued)

FOREIGN PATENT DOCUMENTS

AU    620691 B2    2/1992
GB    846877 A    8/1960
(Continued)

OTHER PUBLICATIONS

QlickSmart of Australia, Blade Flask Blade Remover and Blade Cassette, QlickSmart Product Literature, http://qlicksmart.com/English/Home.htm, date unknown, 3 pages.
(Continued)

*Primary Examiner* — Anthony Stashick
*Assistant Examiner* — Mollie Impink
(74) *Attorney, Agent, or Firm* — Price Heneveld LLP

(57) ABSTRACT

A device for the application and storage of a sharps device is disclosed here in with the ability to re-sterilize and reuse this device on multiple occasions. This device enables the user to access and store the blade in a safe manner where the chances of accidental puncture are greatly reduced. The device enables the user to store the sharps blade in the device in such a manner that will allow the user to autoclave or sterilize the storage device and the blade at the same time. The device is designed for multiple uses over a wide range of different blades, such as the myriad of surgical blades and blades used in the hobby and crafts arena using X-Acto knife style of blades. When a singular device is used for the storage, application and re-loading of sharps, the user is more familiar with the operation of the device, which leads to more comfort of the user in dealing with sharps blades. Also since the operating room has minimal space to store the necessary tools and devices, when a single device can have multiple uses it is advantageous and space saving.

19 Claims, 5 Drawing Sheets

(58) Field of Classification Search
CPC . A61B 17/3217; A61B 17/3215; A61B 17/32; A45D 27/24
USPC .......................................... 206/363; 30/162
See application file for complete search history.

(56) References Cited

U.S. PATENT DOCUMENTS

| | | |
|---|---|---|
| D194,087 S | 11/1962 | Jenkins |
| D194,418 S | 1/1963 | Gaspar |
| 3,380,573 A | 4/1968 | Gulotta |
| 3,442,378 A | 5/1969 | Wolfe |
| 3,696,920 A | 10/1972 | Lahay |
| 3,785,544 A | 1/1974 | Smith |
| D231,714 S | 5/1974 | Arthur |
| 3,916,448 A | 11/1975 | Hamel |
| 3,921,289 A | 11/1975 | Hasegawa |
| D248,871 S | 8/1978 | Forsman et al. |
| 4,106,620 A | 8/1978 | Brimmer et al. |
| D249,362 S | 9/1978 | Forsman et al. |
| 4,120,397 A | 10/1978 | Neumann |
| 4,168,777 A | 9/1979 | Gaskell et al. |
| 4,173,071 A | 11/1979 | Ishida |
| 4,180,162 A | 12/1979 | Magney |
| 4,270,416 A | 6/1981 | Thompson |
| 4,318,473 A | 3/1982 | Sandel |
| 4,386,457 A | 6/1983 | Coombs |
| 4,395,807 A | 8/1983 | Eldridge, Jr. et al. |
| D273,615 S | 4/1984 | Maskrey |
| 4,466,539 A | 8/1984 | Frauenhoffer |
| D275,833 S | 10/1984 | Malpass |
| D276,462 S | 11/1984 | Villarreal |
| 4,730,376 A | 3/1988 | Yamada |
| 4,746,016 A | 5/1988 | Pollak et al. |
| 4,903,390 A | 2/1990 | Vidal et al. |
| 4,930,234 A | 6/1990 | Schmidt |
| 4,971,271 A | 11/1990 | Sularz |
| 4,998,334 A | 3/1991 | Pemberton et al. |
| 5,024,326 A | 6/1991 | Sandel et al. |
| 5,036,866 A | 8/1991 | Eldrige, Jr. et al. |
| D319,873 S | 9/1991 | Rouse |
| 5,071,426 A | 12/1991 | Dolgin et al. |
| 5,088,173 A | 2/1992 | Kromer et al. |
| D327,743 S | 7/1992 | Frenkel et al. |
| D328,026 S | 7/1992 | Stenstrom |
| 5,163,553 A | 11/1992 | Cantwell et al. |
| 5,193,678 A | 3/1993 | Janocik et al. |
| D334,973 S | 4/1993 | Valentine et al. |
| 5,207,696 A | 5/1993 | Matwijcow |
| D337,830 S | 7/1993 | Coyne et al. |
| D341,883 S | 11/1993 | Jones et al. |
| D343,687 S | 1/1994 | Houghton et al. |
| 5,275,606 A | 1/1994 | Abidin et al. |
| 5,299,357 A | 4/1994 | Wonderley et al. |
| 5,312,429 A | 5/1994 | Noack |
| 5,330,492 A | 7/1994 | Haugen |
| 5,330,494 A | 7/1994 | Van Der Westhuizen et al. |
| D349,204 S | 8/1994 | Lefebvre |
| 5,346,677 A | 9/1994 | Risk |
| 5,361,902 A | 11/1994 | Abidin et al. |
| 5,363,958 A | 11/1994 | Horan |
| 5,370,654 A | 12/1994 | Abidin et al. |
| D355,513 S | 2/1995 | Posenauer |
| 5,417,704 A | 5/1995 | Wonderley |
| 5,431,672 A | 7/1995 | Cote et al. |
| 5,433,321 A | 7/1995 | Abidin et al. |
| 5,449,068 A | 9/1995 | Gharibian |
| D366,527 S | 1/1996 | Paterson |
| 5,482,067 A | 1/1996 | Wittrock et al. |
| D369,295 S | 4/1996 | Kobari et al. |
| 5,527,329 A | 6/1996 | Gharibian |
| D372,782 S | 8/1996 | Spehalski |
| 5,374,282 A | 10/1996 | Hoftman |
| 5,569,281 A | 10/1996 | Abidin et al. |
| 5,571,127 A | 11/1996 | Decampli |
| D376,647 S | 12/1996 | Marsh et al. |
| D378,408 S | 3/1997 | Pyeatt et al. |
| 5,662,221 A | 9/1997 | Abidin et al. |
| 5,662,669 A | 9/1997 | Abidin et al. |
| 5,667,067 A | 9/1997 | Gabriel |
| 5,683,407 A | 11/1997 | Jolly et al. |
| D387,177 S | 12/1997 | Davis |
| 5,699,908 A | 12/1997 | Frye et al. |
| 5,706,942 A | 1/1998 | Vila et al. |
| 5,729,879 A | 3/1998 | Hoftman |
| 5,741,289 A | 4/1998 | Jolly et al. |
| 5,752,968 A | 5/1998 | Jolly et al. |
| 5,765,470 A | 6/1998 | Sitro |
| 5,791,472 A | 8/1998 | Davis |
| 5,792,162 A | 8/1998 | Jolly et al. |
| 5,827,309 A | 10/1998 | Jolly et al. |
| D402,767 S | 12/1998 | Davis et al. |
| 5,868,771 A | 2/1999 | Herbert et al. |
| 5,875,532 A | 3/1999 | Musgrave et al. |
| 5,875,533 A | 3/1999 | Henry |
| 5,938,027 A | 8/1999 | Soroff et al. |
| 5,938,676 A | 8/1999 | Cohn et al. |
| 5,941,892 A | 8/1999 | Cohn et al. |
| 5,964,161 A | 10/1999 | Conway |
| 5,968,663 A | 10/1999 | Muggli |
| 6,212,803 B1 | 4/2001 | Key |
| 6,216,868 B1 | 4/2001 | Rastegar et al. |
| D441,192 S | 5/2001 | Park |
| 6,254,621 B1 | 7/2001 | Shackelford et al. |
| D449,685 S | 10/2001 | Morrison |
| D450,130 S | 11/2001 | Goldstein |
| D450,391 S | 11/2001 | Hunt et al. |
| 6,426,041 B1 | 7/2002 | Smith |
| 6,589,258 B2 | 7/2003 | Pilo et al. |
| D479,328 S | 9/2003 | Reynolds et al. |
| 6,626,925 B2 | 9/2003 | Newman et al. |
| D481,129 S | 10/2003 | DiCesare et al. |
| 6,629,985 B1 | 10/2003 | Kiehne |
| D482,788 S | 11/2003 | Montgomery et al. |
| 6,645,216 B2 | 11/2003 | Masury et al. |
| D483,123 S | 12/2003 | Montgomery et al. |
| D489,454 S | 5/2004 | Koseki |
| D490,153 S | 5/2004 | Montgomery et al. |
| 6,757,977 B2 | 7/2004 | Dambal et al. |
| D504,175 S | 4/2005 | Westbrook |
| 6,955,002 B2 | 10/2005 | Sandel et al. |
| 7,036,660 B1 | 5/2006 | Abidin et al. |
| 7,070,051 B2 | 7/2006 | Kanner et al. |
| D528,206 S | 9/2006 | Bierman |
| D535,026 S | 1/2007 | Griffin et al. |
| 7,155,795 B2 * | 1/2007 | Abidin ............... A61B 17/3215 29/426.5 |
| 7,156,231 B1 | 1/2007 | Austria |
| 7,159,713 B1 | 1/2007 | Austria |
| 7,172,611 B2 | 2/2007 | Harding et al. |
| 7,201,760 B2 | 4/2007 | Masury et al. |
| 7,207,999 B2 | 4/2007 | Griffin et al. |
| D542,415 S | 5/2007 | Sandel |
| D544,600 S | 6/2007 | Wentling |
| D549,327 S | 8/2007 | Aparici et al. |
| 7,303,568 B2 | 12/2007 | Jannot |
| D561,898 S | 2/2008 | Goto |
| 7,346,989 B2 | 3/2008 | Shi |
| D568,475 S | 5/2008 | Sandel et al. |
| D568,491 S | 5/2008 | Koseki |
| D568,492 S | 5/2008 | Koseki |
| D568,493 S | 5/2008 | Koseki |
| 7,398,880 B2 | 7/2008 | Henry |
| 7,441,655 B1 | 10/2008 | Hoftman |
| D583,821 S | 12/2008 | Richter |
| 7,458,177 B2 | 12/2008 | Sandel et al. |
| D596,311 S | 7/2009 | Antons |
| D608,015 S | 1/2010 | Sandel |
| D608,456 S | 1/2010 | Sandel |
| D612,050 S | 3/2010 | Baynham |
| D616,089 S | 5/2010 | Van Der Stappen |
| 7,713,280 B2 | 5/2010 | Marshall et al. |
| D618,821 S | 6/2010 | Larsen |
| D621,502 S | 8/2010 | Downs |
| D630,317 S | 1/2011 | Wung |

(56) References Cited

U.S. PATENT DOCUMENTS

| | | |
|---|---|---|
| D636,894 S | 4/2011 | Tomes et al. |
| D638,137 S | 5/2011 | Gross et al. |
| D638,940 S | 5/2011 | Palmer et al. |
| RE42,507 E | 6/2011 | Wilkinson et al. |
| D648,852 S | 11/2011 | Shi |
| D650,912 S | 12/2011 | Tomes et al. |
| 8,114,103 B2 | 2/2012 | Rasco |
| 8,156,653 B2 | 4/2012 | Austria et al. |
| 8,205,340 B2 | 6/2012 | Austria et al. |
| D662,989 S | 7/2012 | Vulgamott et al. |
| D676,146 S | 2/2013 | Austria |
| D676,573 S | 2/2013 | Austria |
| 8,372,503 B2 | 2/2013 | Austria et al. |
| D683,407 S | 5/2013 | Austria |
| D683,452 S | 5/2013 | Davies et al. |
| D703,626 S | 4/2014 | Hermansen |
| D710,497 S | 8/2014 | Pham et al. |
| D712,062 S | 8/2014 | Austria |
| D712,063 S | 8/2014 | Austria |
| D712,064 S | 8/2014 | Austria |
| D713,958 S | 9/2014 | Srinivasan et al. |
| 8,898,910 B2 | 12/2014 | Ichiyanagi et al. |
| 8,931,181 B2 | 1/2015 | Milton et al. |
| 9,113,946 B2 | 8/2015 | Hajgato et al. |
| 2004/0186496 A1 | 9/2004 | Sandel et al. |
| 2004/0243161 A1 | 12/2004 | Kanodia et al. |
| 2005/0065541 A1 | 3/2005 | Abidin et al. |
| 2005/0204932 A1 | 9/2005 | Tingley |
| 2005/0223640 A1 | 10/2005 | Hall et al. |
| 2005/0228420 A1* | 10/2005 | Harding ............ A61B 17/3213 606/167 |
| 2006/0027104 A1 | 2/2006 | Perez, Jr. |
| 2006/0041267 A1 | 2/2006 | Henry |
| 2006/0100650 A1 | 5/2006 | Kiehne |
| 2006/0212058 A1 | 9/2006 | Djordjevic et al. |
| 2007/0039844 A1 | 2/2007 | Zyzelewski et al. |
| 2007/0039845 A1 | 2/2007 | Kaforey et al. |
| 2007/0255298 A1 | 11/2007 | Djordjevic et al. |
| 2007/0265651 A1 | 11/2007 | Yi et al. |
| 2008/0173187 A1 | 7/2008 | Baker |
| 2008/0272023 A1 | 11/2008 | McCormick et al. |
| 2009/0192538 A1 | 7/2009 | Sandel et al. |
| 2009/0267717 A1 | 10/2009 | Baskett |
| 2010/0137894 A1 | 6/2010 | Ueno et al. |
| 2010/0228274 A1 | 9/2010 | Baid |
| 2010/0268258 A1 | 10/2010 | Maxwell |
| 2012/0245610 A1 | 9/2012 | Hajgato et al. |
| 2012/0311869 A1* | 12/2012 | Ichiyanagi ......... A61B 17/3213 30/151 |
| 2013/0079804 A1 | 3/2013 | Milton et al. |
| 2013/0245656 A1 | 9/2013 | Austria |
| 2015/0201957 A1 | 7/2015 | Shi |
| 2015/0250492 A1 | 9/2015 | Austria |
| 2016/0095614 A1 | 4/2016 | Austria |

FOREIGN PATENT DOCUMENTS

| | | |
|---|---|---|
| GB | 2464751 A | 5/2010 |
| JP | 3026909 B2 | 3/2000 |
| JP | 3126664 B2 | 1/2001 |
| JP | 2002177291 A | 6/2002 |
| JP | 2006340857 A | 12/2006 |
| JP | 5390694 B2 | 1/2014 |
| WO | 9424020 A1 | 10/1994 |
| WO | 2008132762 A1 | 11/2008 |
| WO | 2011108099 A1 | 9/2011 |
| WO | 2012002910 A1 | 1/2012 |

OTHER PUBLICATIONS

Smeak, Daniel et al., Core Surgical Skills: Basic Instrument Use, Texas A&M University School of Veterinary medicine and Biomedical Sciences, 2011, pp. 1-9.

Swann-Morton, Surgical Blade removal by Swann-Morton, date unknown, 2 pages.

Trademark Medical, Personal Protective Equipment & Sharps Safety Products: Scalpel Safety, 2010, 2 pages.

The Official Journal of the Anethesia Patient Safety Foundation, APSF Hosts Medication Safety Conference, vol. 25, No. 1, 1-20, 2010, 7 pages.

ADV Medical, Needle Counters Selection, date unknown, 2 pages.

Southmedic, Introducing . . . the only safety scalpel that fits your favorite handle, Safety Cabo, date unkown, 2 pages.

Tyco Healthcare Group LP, Devon* Needle Counters, 2003, 2 pages.

Xodus Medical, Needle Counter and Sharps Disposal Systems, date unknown, 4 pages.

* cited by examiner

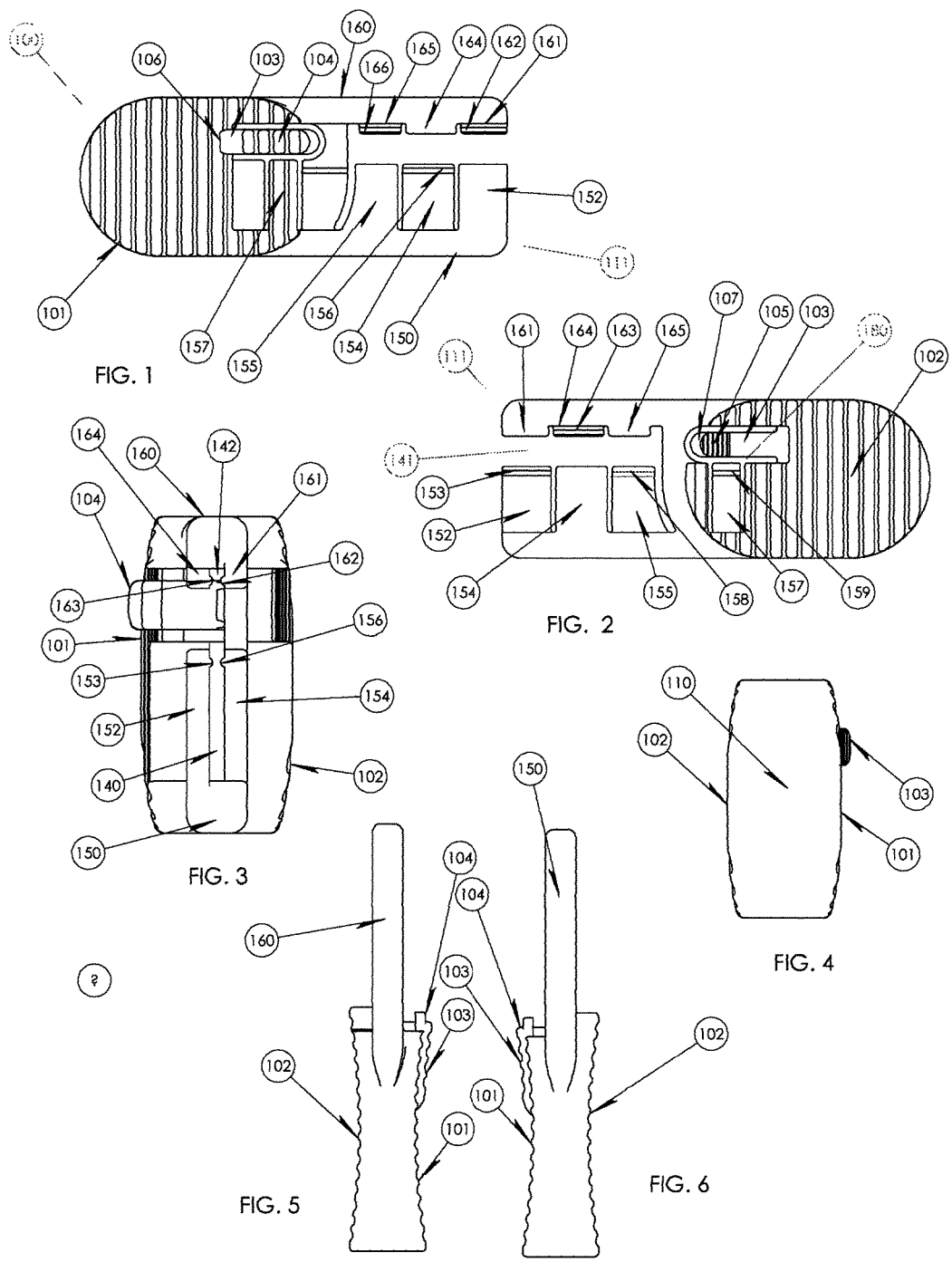

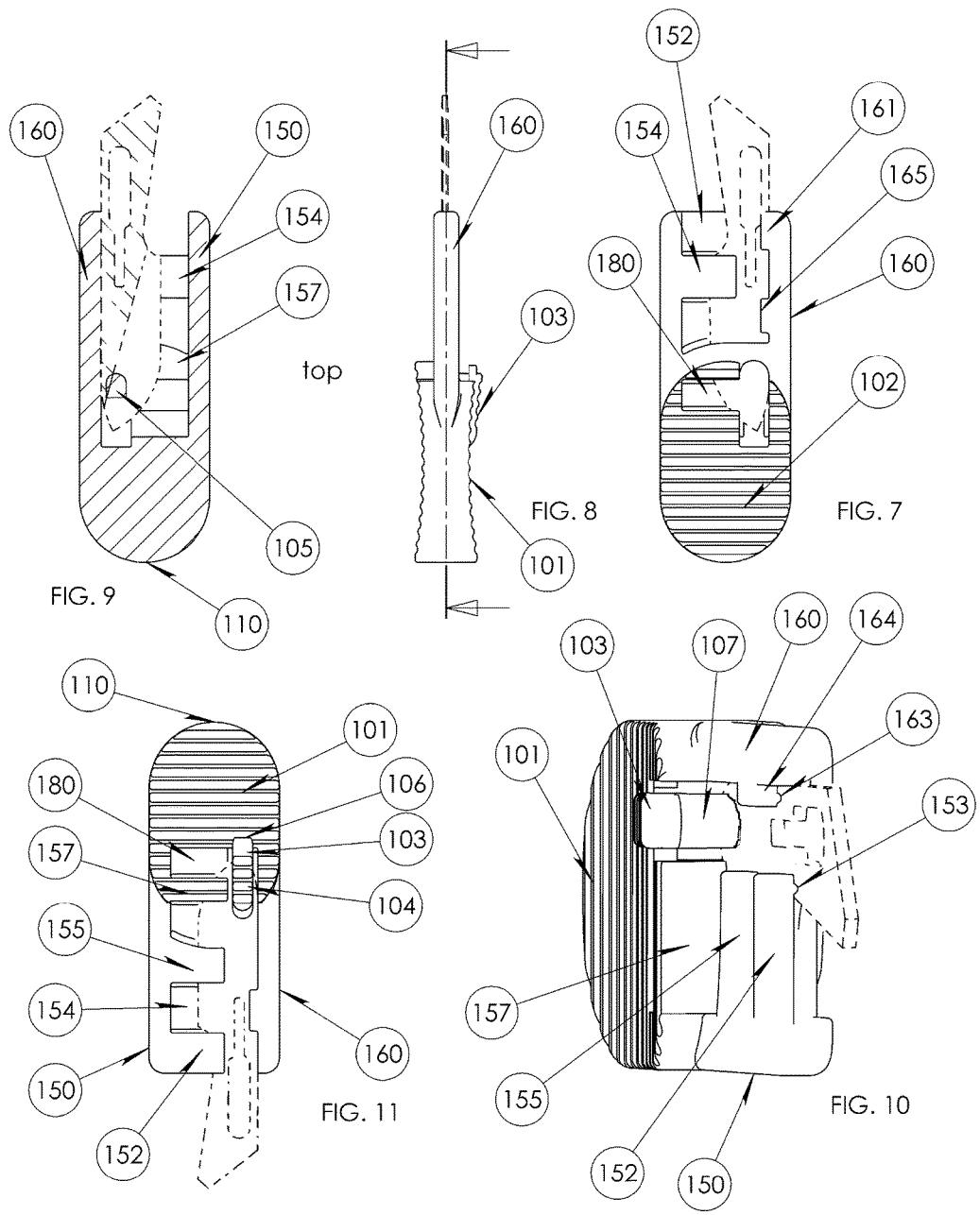

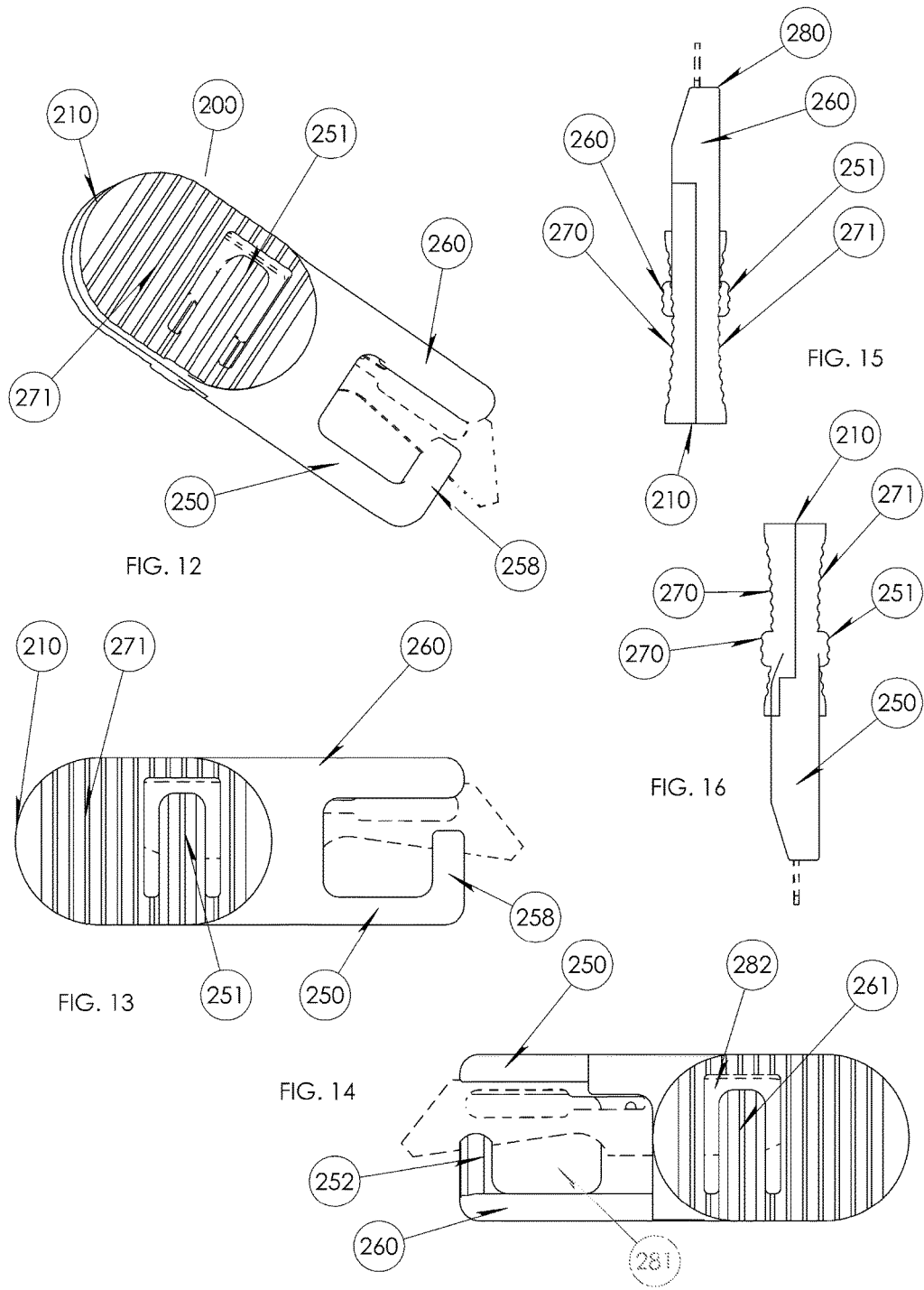

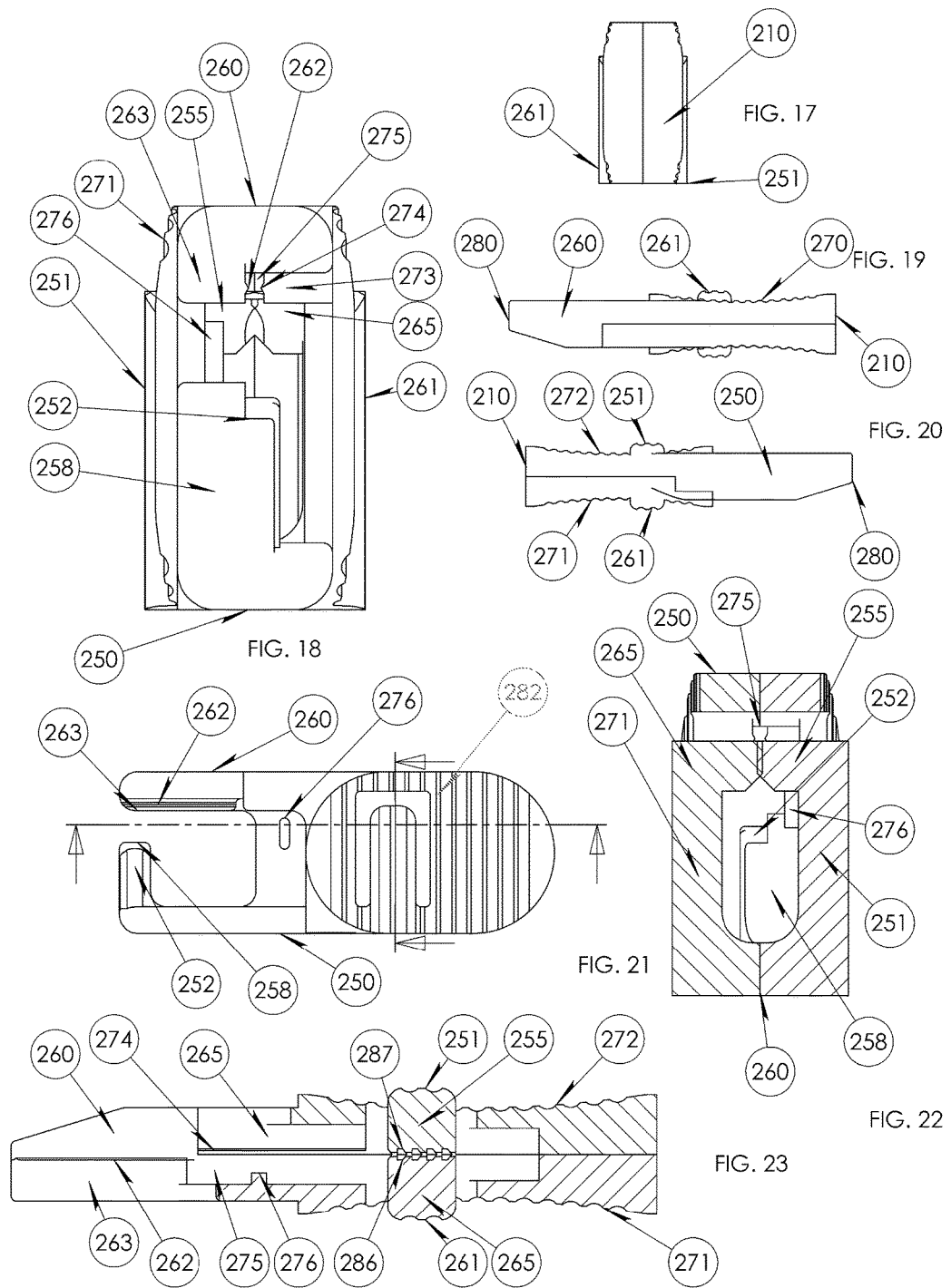

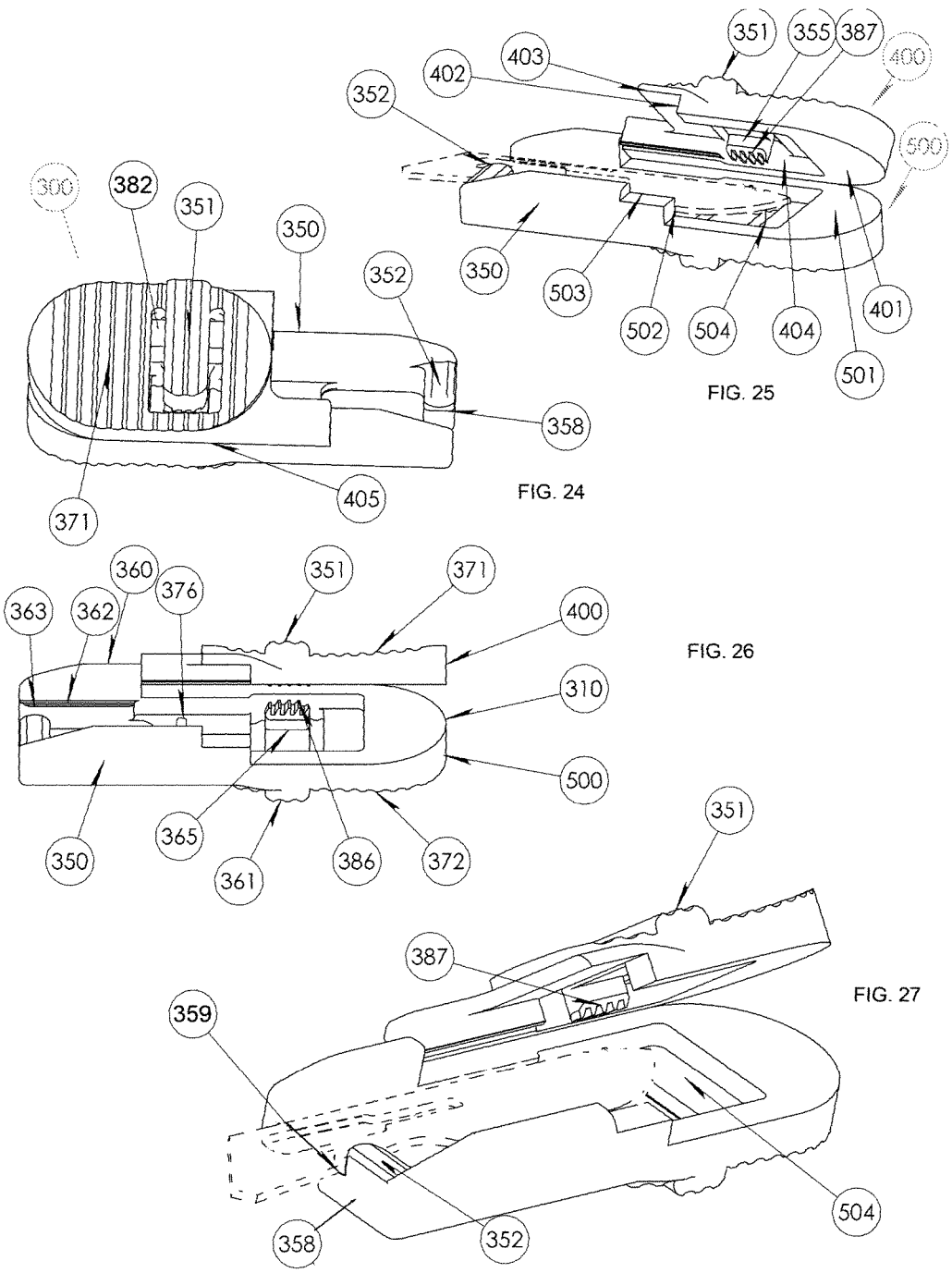

SHARPS BLADE APPLICATOR AND STORAGE DEVICE

CROSS REFERENCE TO RELATED APPLICATION

This application is a continuation of and claims priority to pending U.S. patent application Ser. No. 14/506,554, entitled "SHARPS BLADE APPLICATOR AND STORAGE DEVICE," filed on Oct. 3, 2014, the entire disclosure of which is incorporated herein by reference.

BACKGROUND OF THE INVENTION

This invention covers the field of application where a sharps blade is being transported and getting ready for the user to place a sharp onto a handle. This is particularly applicable to the health care industry where scalpel blades are needing to be attached to handles. It is critical to prevent accidental punctures to have the sharp's blade covered during this application process. Currently few options exist for this dangerous practice.

Summary of the Prior Art and State of the Art

Traditionally, the scalpel blade is packaged individually in sterile pouches. Typically, the medical personnel will open the pouch and let the blade fall into a sterile field as reaching into the pouch to remove the blade would have a high probability of accidental puncture. Once the blade is loose in the sterile field, the personnel will use a clamp or a needle driver to pick up the blade very carefully along the spine of the blade in order to prevent any contact with a sharps portion of the blade. This is particularly difficult with a small scalpel blades such as a number 11 or a number 15.

Another method for the arming of a scalpel, is where the pouch is owned and the user then clamps onto the blade and removes it from the pouch and then inserted onto the handle. This is a dangerous operation as a user's hand is right next to the exposed sharps blade. It is also a very poor practice, though one that is often used, is to use the pouch from which the blade is stored, as the insertion device. It is not an uncommon sight to see one using the pouch as a cover for the sharp for direct attachment by hand of the sharps blade onto the handle. This is a very dangerous and ill advised method as the sharp can easily puncture the pouch and thereby puncture the user. The same is true in the disarming of the scalpel or sharps device. It is also ill advised to use the pouch as the blade protector or as the user attempts to remove the sharps from the handle. The preferred method is to use the needle driver or clamp to remove the blade from the sharps handle. Now you have a blade that is exposed being moved about without any form of protection thereon, which presents a whole new set of dangerous circumstances in the operating room.

To get around the problems associated with using the pouch style of blade delivery, some manufacturers have created a cartridge device whereby the cartridge contains a sharps blade already inserted from the factory. The manufacturer of the cartridge is required to assemble the cartridge and insert the sharp into the cartridge. This is a dangerous process and it is done at the manufacture and not at the place where the sharp is being used. The cartridge with the sharp is usually made of a plastic material which is then sterilized and placed into a sterile pouch. The user then extracts the cartridge from the pouch using their hand as the sharp is completely encased. The cartridge is placed onto the handle and the cartridge is now completely encasing the sharps blade. Some of the cartridge devices can also be used in the disarming of the device. The problem with using the cartridge style device, is that unique or proprietary handles must be used in order to access the blade within the cartridge device. An example of a product with a non-standard blade is U.S. Pat. No. 5,868,771 issued to Herbert et al on Feb. 9, 1999. Furthermore, using the cartridge device does not allow for the user to load and reuse the device that is protecting the sharps or what would be called the loader or armer of the handle. The cartridge style does lend itself to be a disposal instrument but is not reusable.

Some of the cartridge blade loaders have incorporated a safety shield design whereby the cartridge becomes a safety shield that protects the user from accidental puncture. This type of device is disclosed in the U.S. Pat. No. 7,207,999 issued to Gaba et al on Apr. 24, 2007, This design only works with the specified handles such that the loader may also function as the safety shield. One cannot take any scalpel handle and it be incorporated into the safety shield design. The safety shield style of cartridge loader has unique handles that are usually not found in non-cartridge loading handles which precludes its universal use amongst various scalpel handles.

Another style of blade loader is a universal loader with a neck assembly. The current state-of-the-art is detailed in Southmedic's Cabo Safety Scalpels product line and disclosed in U.S. Pat. Nos. 8,567,072 and 7,669,337 issued to Yi et al. This type of blade loader is similar to a cartridge type design that'll work universally with existing scalpel handles. With this device the tang of the sharp, which is the and opposite of the piercing point of the sharp, is permanently attached onto a post or fence which is not a part of the sharp's handle. This post is then attached as a secondary piece to the existing handle. The problem associated with this style of blade loader is that the scalpel now has an extension anywhere from ½ inch almost 2 inches in length. This additional piece will throw off the balance or weighting of the handle. Additionally since scalpels are often used in areas that are delicate or confined in nature, the additional length is detrimental to the functioning of the scalpel. The one advantage of the system is that it is able to be used with a variety of scalpels especially those that are common in the industry as it is the post that is modifiable to any style of scalpel. It needs to be noted that surgeons, or others that you scalpels, often develop a certain liking to a particular scalpels handle due to its balance, waiting, tactile feel, and length of the scalpel. Thus it is important to maintain the surgeons feel in the use of the scalpel.

Another style of blade loader is the style that is presented in this disclosure. This incorporates both the universality of using existing scalpel handles but it also incorporates features that prevents the user's hand from being near the sharps portion of the blade. An example of this style of blade loader is disclosed in U.S. Pat. No. 4,180,162 issued to Magney on Dec. 25, 1979. This device is enclosed box where the user inserts a blade handle to retrieve a blade and then reinserts the bladed handle to remove the blade. This is a single use device not suitable for multiple use and does not prevent the contact of the sharps portion of the blade from contact with the lower surface or walls of the device, thereby damaging and dulling the sharp. Prior art also contains disclosure such as from U.S. Pat. No. 5,361,902 to Abidin, U.S. Pat. No. 4,746,016 to Pollack et al, U.S. Pat. No. 4,180,162 to Magney and U.S. Pat. No. 5,363,958 to Horan, where arming devices exist. But either they must use proprietary handles, do not expose the Tang portion of the blade enabling connection to the blade from the tang directly or do not allow for multiple uses and sterilizing through common means.

As mentioned previously there are other sharps devices other than scalpels that can be used with this current applications disclosed invention. In examining the prior art there it are examples that are applicable only to scalpel handles, such as the aforementioned cartridge loaders, but none of the aforementioned style of blade loader can work with any other style of sharps such as an X-Acto knife. And X-Acto knife requires the tang of the blade to be accessible, which is not possible with the cartridge style or neck style of blade loaders. The current disclosed invention enables the user to have a blade loading device which incorporates an open design whereby the user is able to reuse the loader for future uses. The blade is also held in such a manner to prevent accidental puncture of the user and also protects the sharp portion of the sharps device thereby preventing any nicks to the cutting portion of the sharp. The disclosed invention is sterilizable.

BRIEF SUMMARY OF THE INVENTION

The invention as disclosed herein is a universal blade applicator and storage device which is capable of being used by many different types of blades and provides access to the tang of the blade, which is the end opposite of the sharp point of the blade, which is used to interface with a handle that attaches to the blade to become a sharps cutting tool. This device can be used for a wide variety of scalpel blades, and is designed to allow the user to see though the device through multiple portals to identify the contents of the device and to assure that the blade is properly located in the device without contact therewith. The device is also used with craft style sharps, such as X-Acto style of blades thereby creating a universal device for the most common used detachable sharps tool. Accordingly, it is the goal of this invention to create the device whereby one is protected from accidental puncture by a sharps blade. Whether that sharps blade be in a hospital setting or simply in an arts and crafts settings within X-Acto blade, the user must be protected in the insertion or attachment of the blade onto the handle.

It is an object of this invention to create a device that has one opening where the tang of the blade is exposed to allow access during the insertion of the handle as well as to enable the user to reload the blade loader within the sharp.

It is an object of this invention to create a device whereby a sharps blade can be stored using the same device that will be used for its application onto a handle, with said storage device holding the blade in such a manner as to preclude damage to the sharp edge portion of the blade.

It is an object of this invention to create an applicator so that the users hand and fingers are not at risk of accidental puncture while a sharps blade is being inserted into the appropriate handle and that this applicator can be reused for multiple styles of blades as well as for multiple occasions for use.

It is also an object of this invention to create a device that can be used to store a sharps blade in a safe manner, which is capable of being autoclaved or sterilized with the blade in the device.

It is also an object of this invention to have a single device that can be used to store the sharps blade, to aid the user in applying the blade onto the handle, thereby also creating a single device with multiple uses which, in the crowded operating trays, is advantageous.

BRIEF DESCRIPTION OF THE DRAWINGS

In FIG. 1, the left side of the one-button embodiment is shown on in a plan elevation view.

In FIG. 2, the right side of the one-button embodiment is shown in a plan elevation view.

In FIG. 3, the rear elevation view of the one-button embodiment is shown.

In FIG. 4, the frontal elevation view of the one-button embodiment is shown.

In FIG. 5, the top elevation view of the one-button embodiment is shown.

In FIG. 6, the bottom elevation view of the one-button embodiment is shown.

In FIG. 7, the right side elevation view is shown with the addition of a scalpel that has been inserted to show the product in use.

FIG. 8 is a top view of the one-button embodiment where a scalpel has been inserted. FIG. 8 also shows the cross-sectional line that'll be seen in FIG. 9

In FIG. 9, a cross-section view of the one-button body embodiment is shown with a scalpel that has been inserted to show the product in use. The view is from the left side of the device toward the right side of the device.

FIG. 10 is an oblique rear left side elevation of the one-button device with the blade inserted showing the relationship between the sharp and the device.

FIG. 11 is a left side elevation view of the one-button embodiment with a scalpel that has been inserted.

FIG. 12 is a left side oblique elevation view of the two button embodiment of the device with a scalpel being held in place.

FIG. 13 is a left side elevation view of the two button embodiment of the device.

FIG. 14 is a right side elevation view of the two button embodiment of the device.

FIG. 15 is a top view of the two button embodiment of the device with the scalpel in place.

FIG. 16 is a bottom elevation view of the two button embodiment of the device with the scalpel in place.

FIG. 17 is a frontal elevation view of the to button embodiment of the device.

FIG. 18 is a rear view elevation of the two button embodiment of the device.

FIG. 19 is a top view elevation of the two button embodiment of the device.

FIG. 20 is a bottom elevation view of the two button embodiment of the device.

FIG. 21 is a right side elevation of the two button embodiment of the device and details the cross-sectional dividing lines for views in FIGS. 22 and 23.

FIG. 22 is a vertical cross-sectional view detailing the button area.

FIG. 23 is a horizontal cross-sectional view of the button area.

FIG. 24 and is a rear view of the two-piece embodiment of the device.

FIG. 25 is an frontal oblique bottom view of the two-piece device with the top portion hinged open and a blade inserted to show the relationship between the blade and the interior of the device.

FIG. 26 is a bottom view without the blade shall in of the two-piece embodiment with the top portion hinged open.

FIG. 27 is a rearward oblique bottom view of the two-piece embodiment with the blade inserted to show the detail between the blade and the interior of the device

DETAILED DESCRIPTION OF THE INVENTION

This invention as disclosed in the drawings has the principle use in the surgical environment but there exists no limiting language to prevent this invention to be practiced in other fields of use. The invention consists of two main elements, an insertion section and a sharps retention section. This invention is detailed with the use of a sharps device, such as a scalpel, but its use is not limited to scalpel as any sharps device with a detachable blade is disclosed by this application.

FIG. 1 is the left side plan elevation view of one embodiment of the invention. This embodiment has a singular button 103 to hold the sharp in place once inserted into the device. Device 100 consists of an anterior section 110 and a posterior section 111. The anterior section of device 100 consists of a gripping area with anti-slip means which is contoured to accept a user's thumb and forefinger. Left side ribs 101 and right side ribs 102 are but one of the anti-slip mechanisms that can be used which could also include a ribs, cross-hatching, knurling and a textured surface sections. Ribs are preferred but are not exclusive. Also in the anterior section 110 is button 103 which also contains an anti-slip feature 104, on the exterior side of button 103, which aids the user in an environment where fluids are often present. Anti-slip feature 104 in this embodiment has the same ribs as was shown on in ribs 101 and 102. Button 103 is attached to the proximal and using a living hinge 106. On the interior side of button 103 is wedge surface 105 which is set off from the interior surface through wedge 107. Wedge 107 is designed to be an angular section whereby wedge surface 105 is located past the center point of the interior of device 100. This can be seen in FIG. 3 which highlights that wedge 107 and wedge surface 105 in a relaxed non-use state are as past the centerline of the device. When the user inserts the sharp into the device, it is the living hinge 106 resistance to an outward bending moment which creates the force of friction to hold the blade within the device. By design of hinge 106, there is a resistive force to the displacement of the button 103 once the sharp has been inserted. FIG. 4 shows that button 103 extends out from the left side rib area 101. Anterior end 110 in this invention is shown as a rounded surface but this invention is not limited to a rounded surface. FIG. 5 and FIG. 6 are top and bottom views respectively which shows that ribbed section 101 and rib section 102 have a concave shaped surface which enables the user to more firmly grip the device.

This device has four opposing lower blade holding features and three upper blade holding features located in the interior portion of the device. Each of said blade holding features are independent and are constructed to be rigid enough to resist the out word bending of the feature as the blade is inserted such that the blade is held in place due to the resistive nature of the feature. Said features are counter opposing one another and also define interior blade slot 140. Slot 140 is defined as entrance 141 upper slot 142 which is defined by the three upper blade holding features and a lower slot 143 that are defined by the four lower blade holding features. Upper slot 142 is located along the interior side of upper rail 160. The four lower blade holding features in this invention are shown in by feature 152, 155, 154 and 157 in series and each of said features and then aids from the lower rail 151. Each said lower blade holding features has a sharps blade securement means. In this disclosure the blade sharps blade securement means are a series of detent ribs which are located parallel to the spine of the blade. A detent rib makes contact with and holds the blade in position. The detent ribs are respectively 153, 156, 158 and 159. The distance between the counter opposing lower ribs create a gap whereby the blade is held firmly and the lower blade features bending moment will secure the blade within the slots. It is important that the detents do not create a resistive slot thereby possibly touching the sharps portion of the sharp thereby possibly damaging the edge that is critical to the smooth cutting of the sharp. The lower blade holding features contact the middle portion of the sharp approximately equidistant from the spine to the lower sharp edge of the blade. Upper rail 160 has three upper blade holding features 162 164 and 166 in series and each detent feature has an associated detent rib respectively 161, 163 and 165. It is critical that the upper rail 160 is located so that there does not exist any possible contact between the sharps portion of the blade with any of the interior portions of the device, so that there must be a void area of no less than 0.035" where the blade is not in contact with any feature of the device to prevent damage to the sharp edge of the blade.

FIG. 7 is a right side elevation view of the device where a sharp blade has been inserted into the device. Viewing portal 180 details a viewing window which can be defined in any embodiment such that the tip of the blade is visible. The purpose for this is to show that the tip of the blade is not in contact with any perpendicular surface which could have the potential to dull the tip of the blade FIG. 8 is a top plan elevation view where a sharps blade has been inserted into the device. Another purpose is to be able to identify the sharps blade that is contained therein. As this single device in this embodiment can be used for a variety of blades, it is critical that an identification means is used to enable the user to identify the correct blade to use. A cross-sectional line defines the view seen in FIG. 9. FIG. 9 shows wedge surface 105 in contact with the sharps blade to show that the position of the wedge surface is critical that it is not touching any of the sharp portions of the blade. FIG. 9 also shows that the upper and lower blade features do not contact the blade along any of the sharp portions of the blade. It can be seen that the tang of the blade is accessible in this device so as not to preclude any form of handle, such as an X-Acto blade handle, that requires access to the entire tang portion of the blade in order to secure it into the handle. It is one of the features of this device to present a device that is sterilizeable while the blade is inserted into the device. Sterilization can take place repeatedly using an autoclave, ethylene oxide, gamma radiation or similar sterilization methods. The design of the device is devoid of internal voids or pockets which would make sterilization difficult.

In the operation of this device the user inserts the blade ensuring that the spine of the blade is in contact with the upper rail 160. Due to the nature of this design there is no chance for the sharp portion of the blade to be in contact with any of the detents or the holding wedge which precludes any contact of the sharp portion of the blade to avoid possible lead damage to it. It is further noted that there will be no less than a 035" inch gap between the sharps portion of the blade in the interior portion of lower rail 150. When the user needs to use the sharps blade, the user using a forefinger and thumb grasping method, holds the device, whereby the user will apply pressure onto button 103 so that forward progress of the blade will be prohibited. The operator will insert the holder of the handle into the Tang of the blade and using a rearward motion, removes the blade by withdrawing the blade from the device. In this embodiment, the entire tang is accessible for attachment onto a handle and all 4 sides of the tang are exposed for ease of access and to adapt to a variety of blades. As aforementioned, this device can be used for sharps other than for the style of a surgical scalpel where one has a holder which interrelates to the Tang of the blade. This device can be used for those other sharps holders using the same withdrawal action once the handle is secured to the blade. It is an important advantage of this device to have the same device capable of being reused with having to use a secondary loading operations.

FIG. 12 shows the left side of the two-button embodiment of this invention 200, where this embodiment is similar in feature and concept as the one button, but where there are at least two buttons that hold the sharps blade in place once inserted into the device. In this embodiment device 200 has two counter-opposing button wedge surfaces located in the anterior portion of this embodiment. As with the one button device where one button provides friction through contact and pressure onto the blade to prevent movement, the two button device has two opposing button wedge devices 251 on the left side and 260 on the right side where the opposing wedge surfaces 255 and 265 respectively act together to hold the blade through friction and resistive pressure. The anterior end 210 is shown as a rounded surface but does not preclude a flat surface so that this device could be stored or used in a standing or vertical position. The finger gripping area located near the anterior end 210 has a ribbed surface 271 on the left side and 270 on the right side where said surfaces are contoured to accepted a user's finger and thumb. As before in this embodiment, ribs are shown that will increase the anti-slip properties so that the user's fingers do not move. This same concept can be approached by using a gnarled area or a roughened area. This is important as the user is generally using this device and an environment where fluids are present. The posterior end 280 has a defined upper rail 260 and a lower rail 250 as shown in FIGS. 15 and 16 this embodiment has a single pillar 258 located on lower rail 250 and near the distal and the pillar serves as a guide and also serves as a rest with post 252 and post shelf 259 once the blade is inserted through slot 275. FIG. 18 shows a rearview of the posterior end of the device. In this embodiment there are at least two blade holding features in series. As disclosed, the upper rail 260 has a single blade holding feature located on the left side 262 and a blade holding feature on the right side 273 located in the interior portion of the device. The upper rail 260 shall hold the device with no less than 0.035" inch of a void area between the sharp portion of the blade and the interior portion of lower rail 250. Each blade holding feature has a sharps blade securement means as in the previous embodiment, which are shown as detent ribs that are located parallel to the spine of the blade. The detent ribs 262 and 274 respectively makes contact with only the upper portion of the blade along the spine of the blade as the blade is inserted into the device along upper interior rail 275. The spine of the sharp is the edge of the blade opposite the sharp edge of the blade. In this fashion the sharp edge of the blade is not in contact with any objects that could cause damage to the sharp blade. Guidance post 276 is placed to ensure that the blade will not deviate into the walls possibly damaging the sharp edge of the blade during insert and provides positive pressure of the blade against the detent ribs, securing the blade from movement. FIGS. 22 and 23 detail the buttons used in the two button device. Each button 251 and 261 are in contact at rest. Button 251 has hammer portion 255 emanating perpendicular from button 251 which terminates in gripper 287. Likewise, button 261 has hammer 265 terminating in gripper 286. Shown here, grippers 286 and 287 have multiple vertical ribs to increase surface contact pressure and to minimize the area of contact with the actual sharps blade. This does not preclude other such friction means. Since button 251 and 261 are made of plastic material it is the natural resistivity or elasticity of the plastic that will allow the buttons to bend outwardly as the sharp is inserted, and the natural resistivity of the plastic will hold the blade in place through friction.

In operation of the two button embodiment the user will insert the blade through slot 275 with a slight downward angle and then using post 252 and post shelf 259 as a fulcrum will rotate upwardly the blade through the sharps blade securement devices. This will prevent the sharp portion of the blade from being damaged. This spine of the blade will be held along the detents to 262 and 274 and the body of the blade will be held either sharps blade securement devices 286 and 287. When the user wishes to withdraw the blade, the user grasps the anterior end of the device using a thumb and forefinger, pressing upon each of the buttons 251 and 261. The user orients the device whereby the blade holder portion of the handle will interface with the exposed tang of the blade. The user then simply inserts the holder of the handle into the Tang and withdraws the blade with an angular displacement towards the right side of the device enabling the tang of the blade to become removed from post shelf 259 and then removes the blade in a rearward withdrawal action without having the sharp edge of the blade near any surface preventing the chance for damaging the sharp edge.

FIG. 17 which is a view of the proximal end 210 of the device shows that buttons 251 and 261 extend all the way to the lower rail 250 so that this device is able to stand independent lady on a flat surface. This feature is not critical it is a desired feature of this device. This does not preclude the concept of having the button taper into the body so that there does not exist any flat area associated with lower rail 250. It is also noted that distal end 210 is rounded in this disclosure but does not preclude a flattened distal and 210 which would allow the device to be in a vertical orientation for use. As with the other embodiment it is critical that the user be able to see that the blade has been inserted properly and that there is no contact with the sharpest portion of the blade. Viewing window 281 and viewing port 282 serve the purpose of allowing the user to see that the sharps portion the blade is not in contact with any portion of the device. Another purpose is to be able to identify the sharps blade that is contained therein. As this single device in this embodiment can be used for a variety of blades, it is critical that an identification means is used to enable the user to identify the correct blade to use.

Another embodiment of this invention is shown in FIGS. 24 through 27. This is a two-piece device that is similar in method and construction as the aforementioned two button embodiment. The two pieces of this device are created by dividing the device along its longitudinal planar axis and separating an upper portion from the lower portion, and creating an interior recess in each of the two halves. It is not critical that the divided pieces are of the same length, as shown here in, only that an interior recess is formed whereby the user is able to place the blade into the device rather than needing to insert the blade into the device through the posterior opening. This creates a more safe method of reloading and reusing the device. The front In this embodiment, the two pieces are either secured together as shown in FIG. 24 where 405 is a living hinge—attaching the bottom portion 500 to the upper portion 400 or it is also possible for upper portion 400 to have no connection to lower portion 500. Should upper portion 400 have no connection with lower portion 500, is anticipated that the upper portion 400 and or the lower portion 500 can be made with a different color to signify the type of blade that is held therein. Upper piece 400 contains right side button 351 with its associated wedge 355 and gripping element 387. This two-piece and bought event has a rounded anterior and 310 and a posterior region 380 into which the blade will enter the device. Rail 350 defines the bottom rail of the device and upper rail 360 which contains sharps blade securement device 363 and detent rib 362. As noted that, similar to the two button embodiment, there are contoured areas 371 and 372 which are on the right and left side of the anterior portion of the device 310, said contoured areas matching a thumb and forefinger grasp of the user 362, and contained as part of contour areas 371 and 372, there is button 351 and button 361 respectively. Each button has an associated wedge as well as a gripping element. Upper portion 400 does not incorporate the entire upper section in this design but nothing precludes a two-piece device of this embodiment where the upper and lower portions are the same in length. In this embodiment upper sealing area 401 mates with lower sealing area 501 along with sealing area 403 interfacing with sealing area 503. Additionally, vertical wall ceiling area 502 interfaces with a matching vertical ceiling wall 402. It is anticipated that once the blade has been inserted into the interior of the device, which is shown in open recess 404 of the upper portion 400 and in lower recess 504 of lower portion 500, that the device will be closed and also sonically welded thereby securing the blade inside of the device. In this method, the user is able to place the blade into the device rather than inserting the bladed through the anterior portion of the device. To make this product, sealing area 401 and 501 and sealing areas 403 and 503 can have small male to female interlocking posts as an alternate securing means, not shown in the drawing, which will interface and will snap the upper portion 400 to the lower portion 500. The user is then able to unlock the upper portion from the lower portion reinsert a new blade and repeat the method steps. This makes this device is reusable and is advantageous over the prior art in this fashion.

As with the two button embodiment, there exists pillar 358 which emanates vertically at the end of rail 350 at the posterior end of the device 380. Associated with pillar 358 is post 352 which is shorter in length than pillar 358 and thereby creates shelf 359 upon which the blade will rest once inserted. As with the two button device when the user wishes to remove the blade, the tang of the blade is inserted into the handle, and the user using a slight rightward motion moves the blade off of the shelf 359 and then removes the blade from the interior of the device. This slight rightward motion guarantees that the lower sharp portion of the blade will not come in contact with any interior or exterior sides of the device, thereby preventing damage to the sharp edge. Anterior end 310 is shown on as a rounded or curved surface. It is another embodiment of this device is to have a flat surface so that the device stands vertically and the users able to use it in that configuration or is able to stand the device up a very crowded operating tray to reduce the space taken by the device. FIG. 26 shows the left side button 361 with its associated wage 365 gripping means 386. As shown previously in FIG. 23 the two gripping areas will meet when the device is in its rest position. Once a blade is present the buttons will naturally bow out and their resistivity of the plastic will secure the blade in place. The presence and location of the blade can be confirmed by viewing the blade through portal 382 which is similar in shape and function as the viewing portal 282. Also it is noted that post 376 serves as a guide as the blade is inserted into the device so that the tip of the blade will not jab which into any of the interior surfaces. As mentioned before with this two-piece device, the user is able to place the blade rather than having to insert the blade into the device.

It can be appreciated by those appropriately skilled in the art that changes, modifications or embodiments can be made to this invention without departing from the spirit, principles, theories, ideas or conceptions that have been disclosed in the foregoing. It is herein recognized that the embodiments disclosed by this description of the best mode of practicing this invention, which will be hereafter described in their full breadth in the claims and equivalents thereof.

What is claimed is:

1. A surgical blade applicator comprising:
a lower portion being contoured to accept a finger and a thumb of a user;
an upper portion being contoured to accept the finger and the thumb of the user, the upper portion being operably coupled with the lower portion and moveable relative thereto;
an interior portion having a blade securement feature configured to contact only an upper portion of a blade proximate a spine and a tang of the blade and maintain a gap between a sharp portion of the blade and the interior portion, where said applicator resists contact between the interior portion of said applicator and the blade during insertion or removal of the blade, wherein the removal of the blade is accomplished by withdrawing the blade along an angular displacement path;
a posterior portion configured to receive the blade while allowing exposure of the tang of the blade; and
a viewing portal extending through said applicator on an axis perpendicular to a planar extent of the blade, the viewing portal exposing a cutting edge of the blade to provide visual confirmation that the cutting edge of the blade is spaced at least a minimal distance from the interior portion and to easily identify the blade secured therein, wherein the viewing portal is disposed within an anterior portion and includes a gripping area.

2. The surgical blade applicator of claim 1, further comprising:
the anterior portion defining a flat surface such that a longitudinal extent of said applicator can be aligned vertically during use.

3. The surgical blade applicator of claim 1, wherein the gripping area includes at least one of ribs, cross-hatching, knurling, and raised texturing.

4. The surgical blade applicator of claim 1, further comprising:
a resistive button disposed on at least one of the upper portion and the lower portion.

5. The surgical blade applicator of claim 1, wherein the upper portion and the lower portion are pivotally coupled via a living hinge and configured to interlock via complementary posts on each of the upper portion and the lower portion.

6. The surgical blade applicator of claim 1, wherein at least one of the upper portion and the lower portion includes a concave portion that is contoured to accept the finger and the thumb.

7. A surgical blade applicator comprising:
an anterior portion including a gripping surface and a resistive button;

an interior portion having a blade securement feature configured to contact only an upper portion of the blade proximate a spine and a tang of the blade, wherein the anterior portion of said applicator includes a void defining a space between the interior portion of said applicator and the blade during insertion or removal of the blade, wherein the removal of the blade is accomplished by withdrawing the blade along an angular displacement path;

a posterior portion configured to receive the blade while allowing exposure of the tang of the blade; and a viewing portal extending through said applicator on an axis perpendicular to a planar extent of the blade, the viewing portal disposed within the anterior portion and includes a gripping area exposing a cutting edge of the blade to provide visual confirmation that the cutting edge of the blade is spaced at least a minimal distance from the interior portion and to easily identify the blade secured therein.

8. The surgical blade applicator of claim 7, wherein the anterior portion is a flat surface to facilitate the vertical placement of said applicator upon a horizontal surface.

9. The surgical blade applicator of claim 7, wherein the anterior portion has a curved surface.

10. The surgical blade applicator of claim 7, wherein the gripping area includes at least one of ribs, cross-hatching, knurling, and raised texturing.

11. The surgical blade applicator of claim 7, wherein the tang is exposed and is directly accessible to a sharps handle.

12. The surgical blade applicator of claim 7, further comprising:

an upper portion and a lower portion, wherein the upper portion and the lower portion are pivotally coupled via a living hinge and configured to interlock via complementary posts on each of the upper portion and the lower portion.

13. A surgical blade applicator comprising:

an anterior portion contoured to accept a finger and thumb of a user and including a resistive button;

an interior portion having one or more detent ribs configured to contact only an upper portion of the blade proximate a spine and a tang of the blade, wherein the detent ribs are located parallel to the spine of the blade and wherein the removal of the blade is accomplished by withdrawing the blade along an angular displacement path;

a void defined within the interior portion that provides sufficient space within said applicator such that a cutting edge of the blade is free of contact with any portion of said applicator during insertion and during removal of the blade from said applicator; and a viewing portal extending through said applicator on an axis perpendicular to a planar extent of the blade, the viewing portal exposing a cutting edge of the blade to provide visual confirmation that the cutting edge of the blade is spaced at least a minimal distance from the interior portion and to easily identify the blade secured therein.

14. The surgical blade applicator of claim 13, wherein said applicator includes an upper portion and a lower portion, and wherein said applicator is designed to allow the user to separate a right side portion of said applicator from a left side portion of said applicator along its longitudinal plane bisecting perpendicularly through an upper rail and a lower rail, wherein one of the upper or lower portions can be detached from contact with the other of the upper or lower portion, thereby allowing a new blade to be positioned within the interior portion of said applicator while the upper and lower portions are detached.

15. The surgical blade applicator of claim 14, wherein the upper portion and the lower portion of said applicator are attached by a living hinge.

16. The surgical blade applicator of claim 13, wherein the anterior portion defines a flat surface to facilitate vertical alignment of said applicator upon a horizontal surface.

17. The surgical blade applicator of claim 13, wherein the anterior portion defines a concave surface.

18. The surgical blade applicator of claim 13, further comprising:

a gripping surface that includes at least one of ribs, cross-hatching, knurling, and raised texturing.

19. The surgical blade applicator of claim 13, further comprising:

a posterior portion configured to receive the blade while allowing exposure of the tang of the blade.

* * * * *